(12) United States Patent
Brown

(10) Patent No.: US 11,730,235 B2
(45) Date of Patent: Aug. 22, 2023

(54) HEEL INTEGRATION FOR A SHOE

(71) Applicant: Timesha Brown, Mt. Morris, MI (US)

(72) Inventor: Timesha Brown, Mt. Morris, MI (US)

( * ) Notice: Subject to any disclaimer, the term of this patent is extended or adjusted under 35 U.S.C. 154(b) by 0 days.

(21) Appl. No.: 16/943,725

(22) Filed: Jul. 30, 2020

(65) Prior Publication Data

US 2021/0030114 A1    Feb. 4, 2021

Related U.S. Application Data

(60) Provisional application No. 62/881,053, filed on Jul. 31, 2019.

(51) Int. Cl.
| | |
|---|---|
| *A43B 21/26* | (2006.01) |
| *A43B 21/32* | (2006.01) |
| *A43B 21/42* | (2006.01) |
| *A43B 21/06* | (2006.01) |
| *A43B 21/24* | (2006.01) |
| *A43B 23/08* | (2006.01) |
| *A61F 5/01* | (2006.01) |
| *A43B 21/36* | (2006.01) |

(52) U.S. Cl.
CPC .............. *A43B 21/26* (2013.01); *A43B 21/32* (2013.01); *A43B 21/06* (2013.01); *A43B 21/24* (2013.01); *A43B 21/36* (2013.01); *A43B 21/42* (2013.01); *A43B 23/088* (2013.01); *A61F 5/0111* (2013.01); *A61F 5/0127* (2013.01); *A61F 5/0195* (2013.01)

(58) Field of Classification Search
CPC ......... A43B 21/26; A43B 21/32; A43B 21/42; A43B 21/06; A43B 21/24; A43B 21/36; A43B 23/088; A61F 5/0111; A61F 5/0127; A61F 5/0195

USPC ......................................................... 36/34 R
See application file for complete search history.

(56) References Cited

U.S. PATENT DOCUMENTS

| | | | | |
|---|---|---|---|---|
| 1,206,721 | A * | 11/1916 | Laurie .................... | A43B 21/32 36/55 |
| 1,926,818 | A * | 9/1933 | Rateliff .................. | A43B 23/28 36/58.5 |
| 1,995,506 | A * | 3/1935 | Guy ........................ | A43B 23/14 36/43 |
| 2,418,342 | A * | 4/1947 | Freedman .............. | A43B 11/02 36/82 |
| 3,373,513 | A * | 3/1968 | Jewell .................... | A43B 13/34 36/58.5 |
| 4,179,826 | A * | 12/1979 | Davidson ............... | A43B 21/32 36/129 |

(Continued)

*Primary Examiner* — Heather Mangine
*Assistant Examiner* — Dakota Marin
(74) *Attorney, Agent, or Firm* — Ward Law Office LLC; Jacob M. Ward

(57) ABSTRACT

A combination, comprising:
a shoe having an upper and a sole, wherein the shoe is configured to cover an instep of a foot of a wearer; and
a heel integration system including an insert having a front end and a back end, the insert configured to be disposed in the shoe, and configured to receive an ankle-foot orthoses brace while the shoe is worn, the insert having a heel portion and an ankle portion, the ankle portion having a curved wall with at least one bulge formed therein,
wherein the bulge is created from an indentation formed on an interior surface of the ankle portion which forms a protrusion on an exterior surface of the ankle portion.

6 Claims, 6 Drawing Sheets

(56) References Cited

U.S. PATENT DOCUMENTS

| | | | | |
|---|---|---|---|---|
| 4,325,380 A * | 4/1982 | Malkin | | A43B 21/32 36/140 |
| 4,942,677 A * | 7/1990 | Flemming | | A43B 13/127 36/35 R |
| 5,015,427 A * | 5/1991 | Sosnow | | A43B 21/32 36/71 |
| 5,127,170 A * | 7/1992 | Messina | | A43B 23/08 36/105 |
| 5,226,875 A * | 7/1993 | Johnson | | A43B 7/20 36/114 |
| 5,396,718 A * | 3/1995 | Schuler | | A43B 21/30 36/38 |
| 5,449,005 A * | 9/1995 | Echols | | A43B 7/20 36/89 |
| 6,442,874 B1 * | 9/2002 | Long | | A43B 3/26 36/97 |
| 6,594,921 B2 * | 7/2003 | Laio | | A43C 11/00 36/105 |
| 6,775,927 B2 * | 8/2004 | Glicksman | | A43B 21/52 36/72 B |
| 7,168,188 B2 * | 1/2007 | Auger | | A43B 23/088 36/58.5 |
| 7,267,657 B1 * | 9/2007 | Mitchell | | A61F 5/0193 602/29 |
| 7,793,438 B1 * | 9/2010 | Busse | | A43B 11/02 36/105 |
| 7,867,184 B2 * | 1/2011 | Mitchell | | A61F 5/0127 602/29 |
| 8,051,586 B2 * | 11/2011 | Auger | | A43B 7/20 36/103 |
| 8,251,936 B2 * | 8/2012 | Fout | | A61F 5/0195 36/25 R |
| 9,161,593 B2 * | 10/2015 | Larson | | A43B 3/18 |
| 9,192,502 B2 * | 11/2015 | Drillio | | A61F 5/0127 |
| 9,770,357 B2 * | 9/2017 | Nayfa | | A43B 7/20 |
| 9,788,596 B2 * | 10/2017 | Schenone | | A43B 3/26 |
| 10,455,899 B2 * | 10/2019 | Chang | | A43C 7/00 |
| 11,224,263 B2 * | 1/2022 | Darby | | A43B 19/00 |
| 2002/0162250 A1 * | 11/2002 | Campbell | | A43B 23/17 36/173 |
| 2003/0200680 A1 * | 10/2003 | Chang | | A43B 3/248 36/105 |
| 2006/0010718 A1 * | 1/2006 | Auger | | A43B 17/18 36/69 |
| 2006/0032091 A1 * | 2/2006 | Kilgore | | A43B 23/17 36/68 |
| 2009/0216167 A1 * | 8/2009 | Harris | | A61F 5/0127 36/89 |
| 2010/0016813 A1 * | 1/2010 | Brown | | A61F 5/30 604/293 |
| 2010/0101112 A1 * | 4/2010 | Powaser | | A43B 1/0072 36/43 |
| 2014/0090273 A1 * | 4/2014 | Piontkowski | | A43B 13/386 36/44 |
| 2014/0202044 A1 * | 7/2014 | Adami | | A43B 7/19 36/34 R |
| 2016/0150852 A1 * | 6/2016 | Cai | | A43B 7/1485 36/88 |
| 2017/0295884 A1 * | 10/2017 | Hung | | A43B 13/36 |
| 2018/0332926 A1 * | 11/2018 | Kramer | | A43B 21/32 |

* cited by examiner

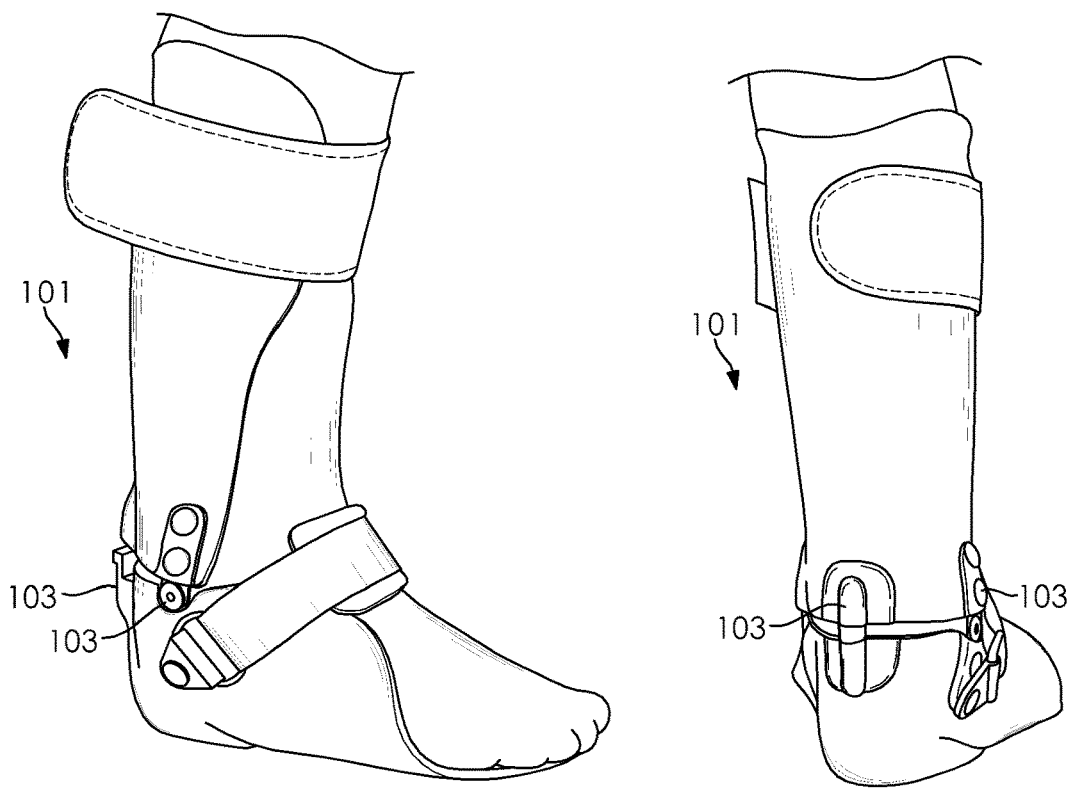
FIG. 13  FIG. 14
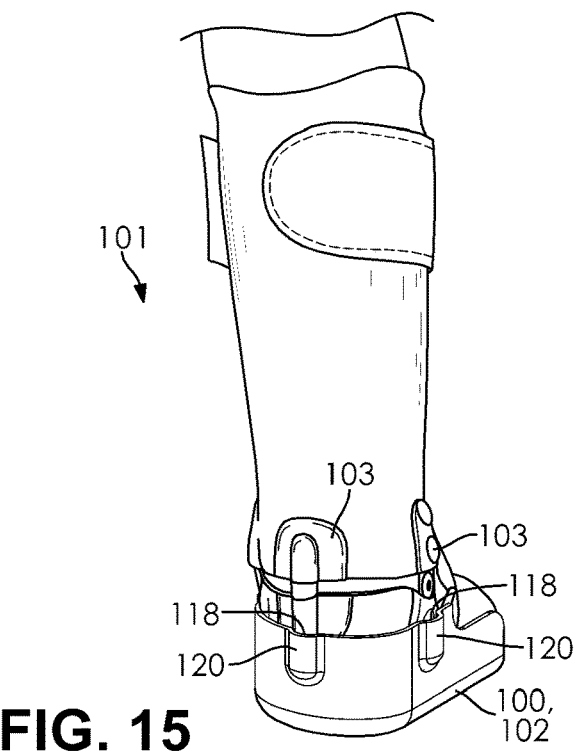
FIG. 15

HEEL INTEGRATION FOR A SHOE

CROSS REFERENCE TO RELATED APPLICATIONS

This application claims the benefit of U.S. Provisional Application Ser. No. 62/881,053, filed on Jul. 31, 2019. The entire disclosure of the above application is hereby incorporated herein by reference.

FIELD

The present disclosure relates generally to shoe inserts, and more particularly, to shoe inserts to facilitate the use of an ankle foot orthosis brace.

BACKGROUND

An ankle foot orthosis (AFO) brace is a support intended to control the position and motion of the ankle, compensate for weakness, or correct deformities. The AFO brace can be used to support weak limbs, or to position a limb with contracted muscles into a more normal position. In addition, AFO braces are used to control foot drop caused by a variety of neurologic and musculoskeletal disorders.

A typical AFO brace creates an L-shaped frame around the foot and ankle, extending from just below the knee to the metatarsal heads of the foot. AFO braces can be purchased off the shelf or can be custom molded to an individual wearer, and can be fabricated of a variety of materials, including heat-moldable plastics, metal, leather and carbon composite. AFO braces are the most commonly used orthoses or orthotics, making up about twenty-six percent (26%) of all such orthoses provided in the United States.

AFO braces are commonly used in wearers suffering from drop foot, which a neural disorder in which one cannot dorsiflex, or raise up, the toes or raise the foot from the ankle. As a result, the foot is stuck in a plantar flexed, i.e., hanging, position and drags on the ground when walking. This condition may be caused by stroke, ALS, muscular dystrophy, multiple sclerosis, cerebral palsy, bone sarcoma, and aplastic paraplegia.

Undesirably, the typical AFO brace adds substantial bulk to the wearer's foot. Accordingly, the wearer may require shoes that are substantially larger than the size of their foot in order to accommodate use of the AFO brace. The larger shoe may also add an undesirable amount of weight to the wearer's foot, which may likewise cause the foot to become stuck in the plantar flexed (hanging) position.

There is a continuing need for a heel integration system that allows a shoe to receive an AFO brace. Desirably, the heel integration system permits a wearer to wear a shoe that is more correctly sized for the wearer.

SUMMARY

In concordance with the instant disclosure, a heel integration system that allows a shoe to receive an AFO brace, and which permits a wearer to wear a shoe that is more correctly sized for the wearer, has been surprisingly discovered.

In one embodiment, a heel integration system for a shoe includes an insert. The insert is configured to be disposed in the shoe and to receive an AFO brace. The insert has a heel portion and an ankle portion. The insert having at least one bulge, wherein the bulge is created from an indentation formed on an interior surface of the ankle portion which forms a protrusion on an exterior surface of the ankle portion. The ankle portion has at least one indentation formed on an interior surface thereof. The indentation is configured to receive at least one projection of the AFO brace upon being received by the insert.

In another embodiment, a combination shoe with heel integration system includes the shoe and an insert. The insert is disposed in the shoe, and the insert is configured to receive an AFO brace. The insert has a heel portion and an ankle portion. The ankle portion has at least one recess formed on an interior surface thereof. The recess configured to receive at least one projection of the AFO brace upon being received by the insert.

In an additional embodiment, a method of using a shoe with a heel integration
system includes provision of measurements of an AFO brace. Next, the method includes a step of providing a conventional shoe. Then, the method includes a step of providing an insert, where the insert is configured to be disposed in the shoe. The insert is configured to receive the AFO brace, and the insert has a heel portion and an ankle portion. The ankle portion has at least one indentation formed therein. The indentation is configured to receive at least one projection of the AFO brace. Then, the method includes a step of removing padding from a heel of the shoe. Next, the method involves a step of installing the insert into the heel of the shoe. The method then includes a step of securing the insert to the shoe. The heel insert is thereby integrated into the shoe and readied for receipt of the AFO brace being worn by the wearer.

DRAWINGS

The above, as well as other advantages of the present disclosure will become readily apparent to those skilled in the art from the following detailed description, particularly when considered in the light of the drawings described hereafter.

Figure 8:
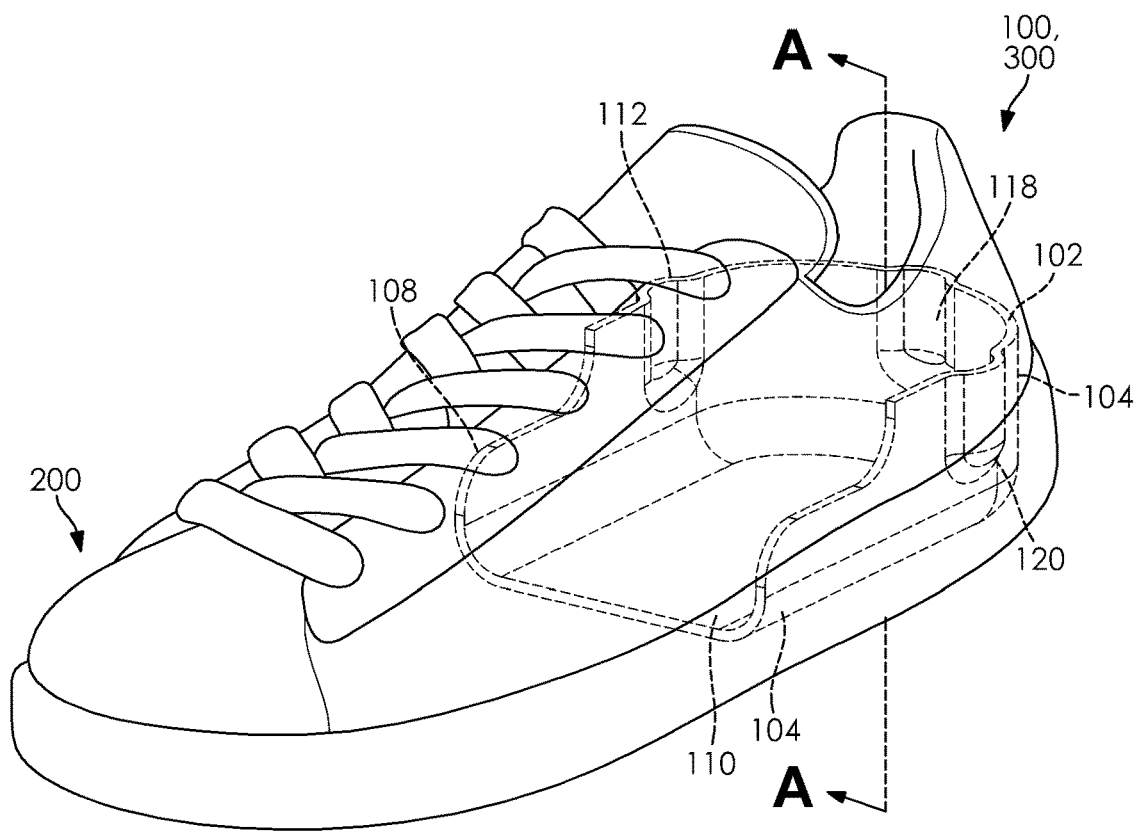
FIG. 8 is a top perspective view of a shoe containing the insert of the heel integration system shown in FIG. 6, and further depicting the installation of the insert within the shoe.
Figure 9:
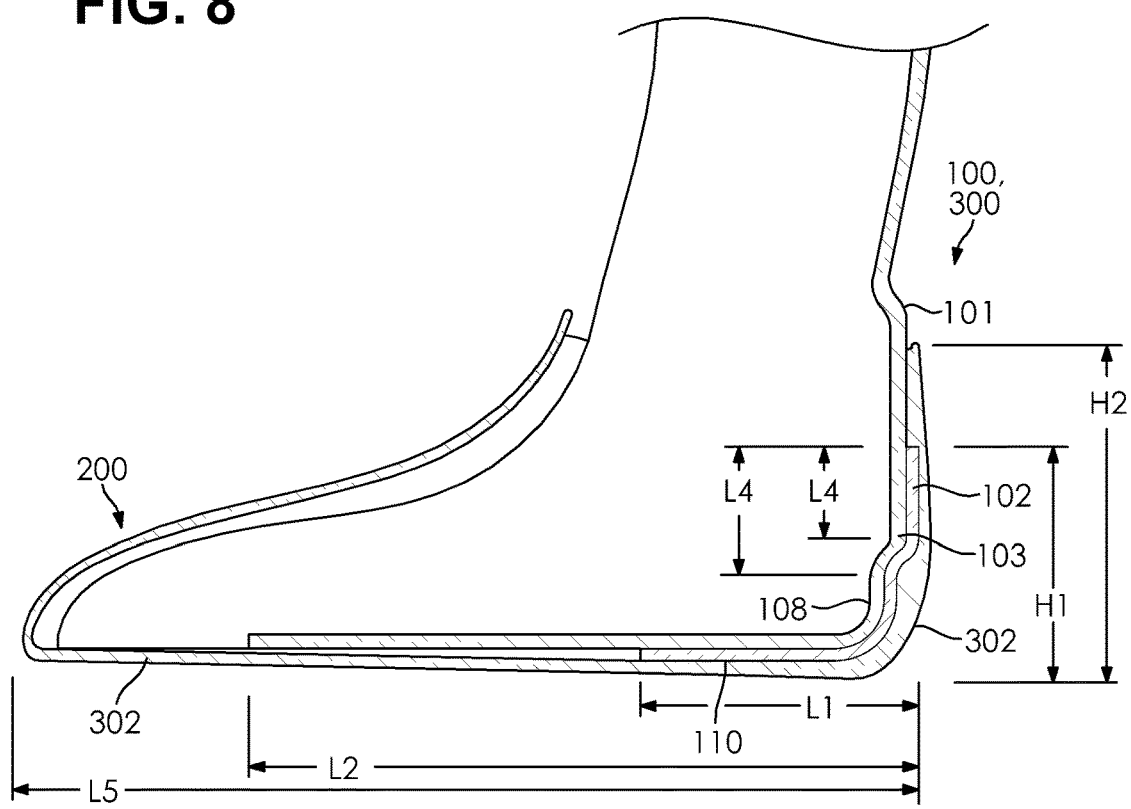
FIG. 9 is a cross sectional, side elevational view of the shoe taken at section line A-A in FIG. 8, and further depicting an interior of the shoe with the heel integration system installed therein.
Figure 10:
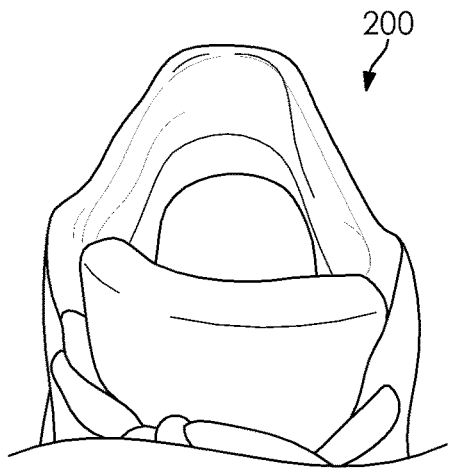
Figure 11:
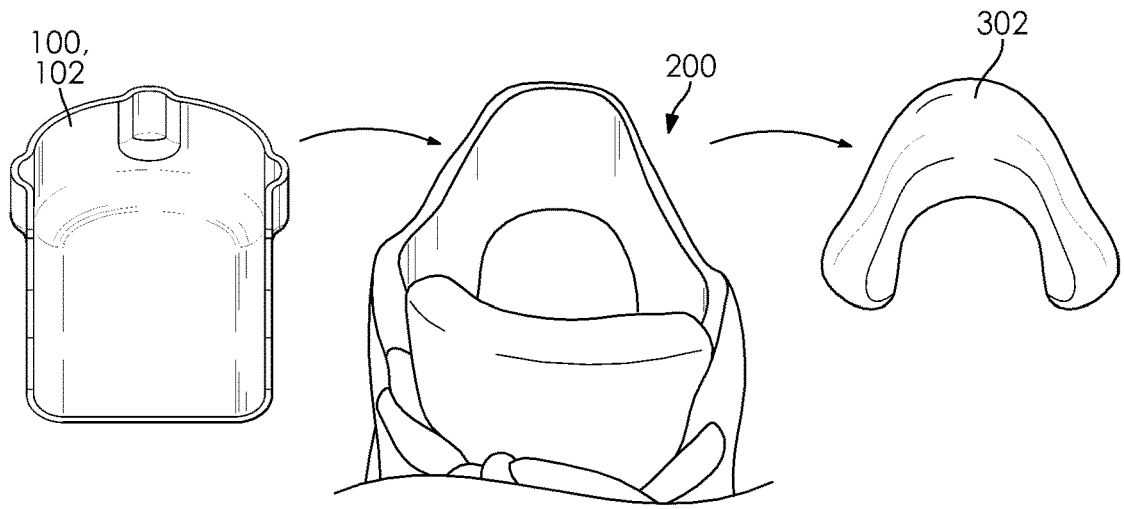
Figure 12:
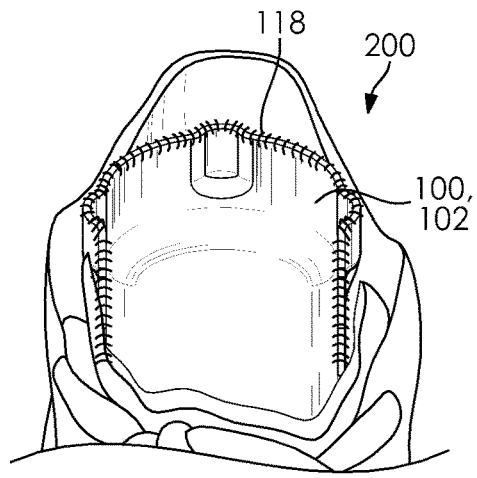
Figure 16:
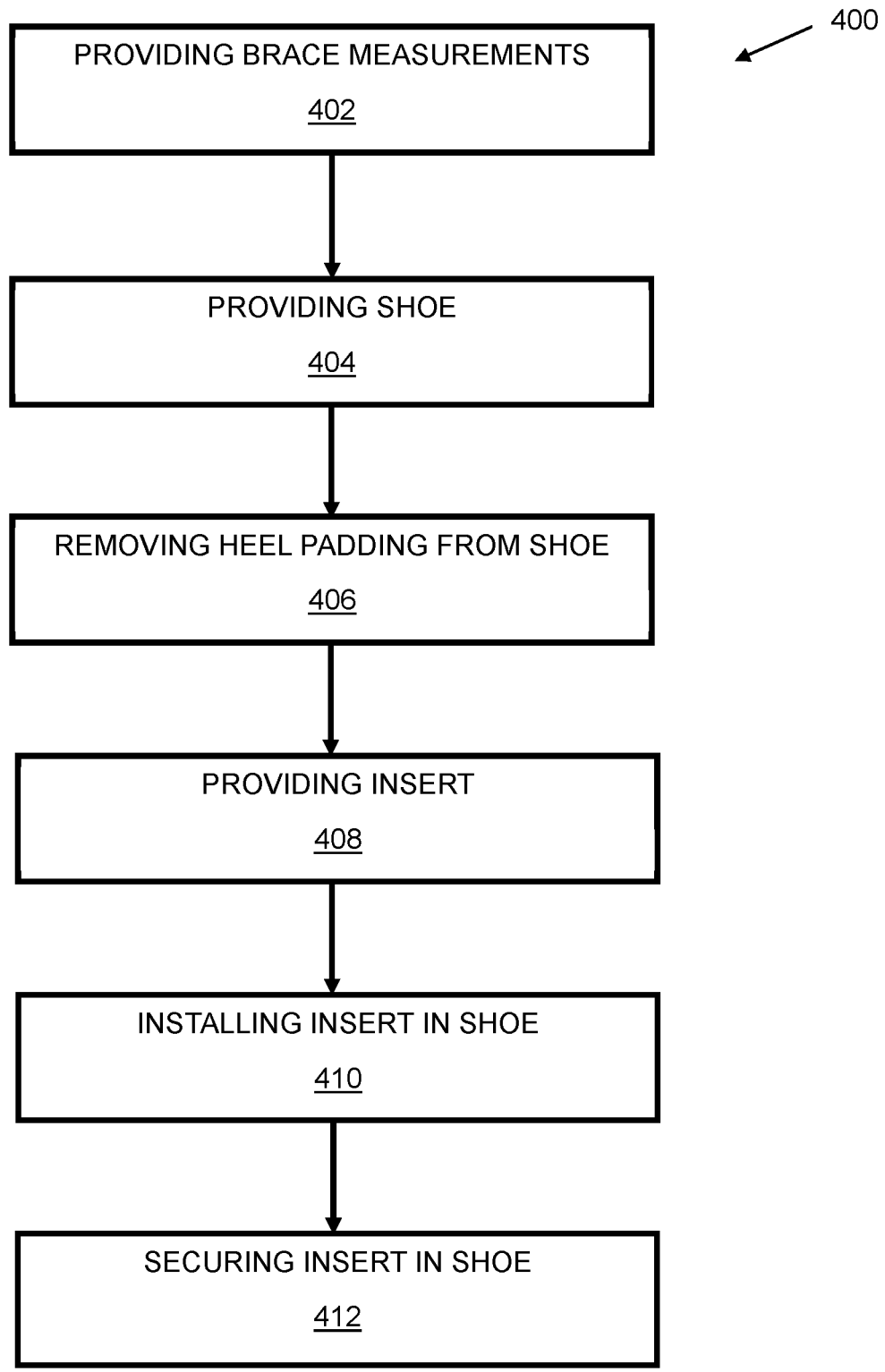

FIGS. 10-12 are top perspective views showing a stepwise installation of the heel integration system shown in FIGS. 5-9, with a conventional shoe without the heel integration system shown in FIG. 10, the heel of the shoe following the removal of padding of the heel shown in FIG. 11, and the installation of the insert of the heel integration system in the heel of the shoe, according to the method of the present disclosure;

FIG. 13 is a front perspective view of a Hinged AFO brace, which may be utilized with the heel integration system of FIGS. 1-9;

FIG. 14 is a rear perspective view of the Hinged AFO brace of FIG. 13;

FIG. 15 is a rear perspective view of the Hinged AFO brace of FIGS. 13-14, further depicting a plurality of projections of the AFO brace disposed in indentations of the insert of the heel integration system; and FIG. 16 is a flowchart illustrating a method for manufacturing the shoe with the heel integration system as shown in FIGS. 10-12.

DETAILED DESCRIPTION

The following description is merely exemplary in nature and is not intended to limit the present disclosure, application, or uses. It should be understood that throughout the drawings, corresponding reference numerals indicate like or corresponding parts and features. In respect of the methods disclosed, the order of the steps presented is exemplary in nature, and thus, is not necessary or critical unless otherwise disclosed.

With reference to FIGS. 1-12, a heel integration system 100 is shown. The heel integration system 100 may be configured to be disposed in a shoe 200 having an upper and a sole, wherein the shoe is configured to cover an instep of a foot of a wearer. The shoe 200 may be a conventional shoe that has been modified to receive the heel integration system 100, as described further herein, or a shoe 200 that has been specially manufactured to receive the heel integration system 100.

It should be appreciated that a typical or conventional shoe includes two main portions: a sole; and an upper. The entire portion of the shoe that is located below a wearer's foot is generally called the sole. The portion of the shoe that covers an upper portion of the wearer's foot is generally called the upper. The sole may include a variety of components such as an insole for creating a layer of comfort between the sole and the wearer's foot, a midsole for shock absorption, and an outsole formed from a durable material for contacting the ground. Likewise, the upper may include a variety of components, such as a toe cap that covers the front of the wearer's foot, a vamp that covers the mid-front of the wearer's foot, and a quarter that covers the rear and sides of the wearer's foot. The toe cap, vamp, and quarter may be sewn together separately, or provided as one or more integral pieces, and together may be referred to as the "body" of the shoe.

Depending on the shoe design employed, the shoe may also have a fastening portion disposed adjacent an aperture in the shoe where the wearer inserts the wearer's foot. The fastening portion may include fasteners such as laces, zippers, and hook and loop fasteners. A tongue may be provided, generally when the shoe includes a fastening portion with laces, and may run along a top-center of the shoe between the fastener and the wearer's foot. The location of the fastener and the tongue is generally referred to as the instep of the shoe.

The typical shoe may also include a variety of other features for affecting the comfort and overall aesthetics of the shoe such as liners, cushions, toe inserts, and design elements for logos and the like. Importantly, the upper of many conventional shoes will have a heel that is disposed at a rear of the shoe body, and which extends upwardly from the sole. The heel is often provided with padding that may be helpful in retaining the shoe on a foot of the wearer, while also supporting the ankle of the wearer and permitting for a comfortable fit. However, the presence of the heel and the associated padding normally makes the insertion of a conventional AFO brace 101 difficult without selecting a shoe size that is significantly greater than the size of shoe that would normally be worn by the wearer.

It should be appreciated that the heel integration system 100 of the present disclosure may be configured to receive a variety of AFO braces 101 of differing shapes and sizes. Likewise, the heel integration system 100 may be scaled to properly fit a predetermined shoe, as desired. For example, the heel integration system 100 may be configured to working with AFO braces 101 commercially available from Surestep, LLC, with offices in South Bend Ind. Surestep provides different models of AFO braces 101 such as Surestep SMO, Toe Walking SMO, Big Shot SMO, Open Heel, Big Shot AFO, Indy 2 Stage, Pullover AFO, Hinged AFO, and Advanced AFO. The Hinged AFO is illustrated in FIGS. 13-14.

As shown in FIGS. 1-12, the heel integration system 100 may include an insert 102. The insert 102 may be configured to be disposed in the shoe. Where the insert 102 is disposed in the shoe, the AFO brace 101 may be received by the insert 102, as described in greater detail hereinbelow.

It should be appreciated that the insert 102 may be fabricated from a suitable durable material. Desirably, the durable material has a sufficiently high impact resistance in order to allow for repeated use of the insert 102 without an undesirable breaking, degradation, or deformation of the insert 102. For example, the durable material may be sufficiently resilient to allow for repeated insertion and removal of the AFO brace 101, without an undesirable degradation of the insert 102 due to friction. Likewise, the durable material should have a sufficiently high fatigue resistance to militate against damage to the insert 102 after torsion, bending, or flexing during use. The durable material may also have a sufficiently high heat resistance to allow for repeated use by the wearer without an undesirable deformation of the insert 102, in operation.

In particular non-limiting embodiments, the durable material may be a plastic material. For example, the plastic material may be one of polycarbonate, acrylonitrile butadiene styrene, polyethylene terephthalate, polypropylene. In another non-limiting example, the durable material may be metal. In further embodiments, the durable material may be a silicone or elastomer material. Advantageously, the insert 102 may be fabricated from a combination of durable materials, in order to reach the desired physical properties of the insert 102.

It should be appreciated that silicone is particularly well suited for the durable material of the present disclosure. In particular, silicone is desirably water resistant and heat resistant, which will allow the insert 102 to withstand long term use. Additionally, silicone is tear resistant, and allows for the insert 102 to be used without an overall degradation or deformation of the shape of the insert 102. A skilled artisan may select other suitable materials for the insert 102, within the scope of the present disclosure.

According to certain embodiments of the present disclosure, the insert 102 may be manufactured by a 3D printing process. Advantageously, a manufacturing of the insert 102 via the 3D printing process allows for customization of the insert 102. The insert 102 may thereby be fabricated to fit a unique AFO brace 101 of the wearer. As each wearer may have a slightly different AFO brace 101, 3D printing allows for minor variations of the insert 102 as needed in order to accommodate the different types of AFO braces 101. A skilled artisan may select other suitable methods to manufacture the insert 102, as desired.

With continued reference to FIGS. 1-12, the insert 102 may include a heel portion 104 and an ankle portion 106. The heel portion 104 and the ankle portion 106 may be co-formed to provide a single, unitary, one-piece unit. The heel portion 104 of the insert 102 may be configured to receive a heel of the AFO brace 101, for example, as shown in FIGS. 8-12. Likewise, the ankle portion 106 may be configured to receive an ankle of the AFO brace 101.

A curvature of the curved side wall 108 may be specially configured to match or correspond with a curvature of the AFO brace 101. For example, the heel portion 104 may have a curved side wall 108. In certain embodiments, as shown in FIG. 9, the insert 102 may have a substantially L-shaped cross section. The L-shaped cross-section may conform closely to the predetermined shoe selected by the wearer.

Figure 3:
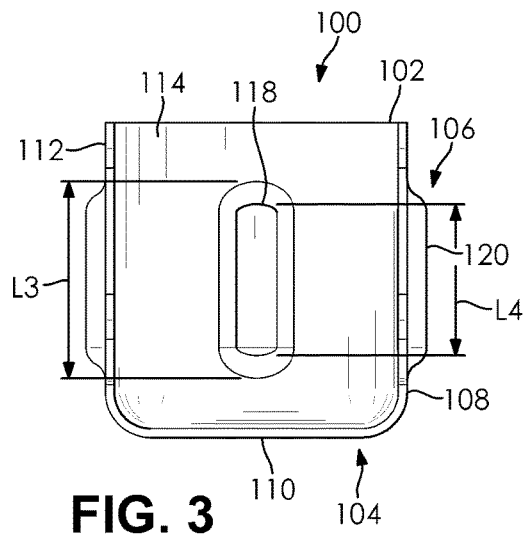
FIG. 3 is a front elevational view of the insert shown in FIG. 1.
Figure 4:
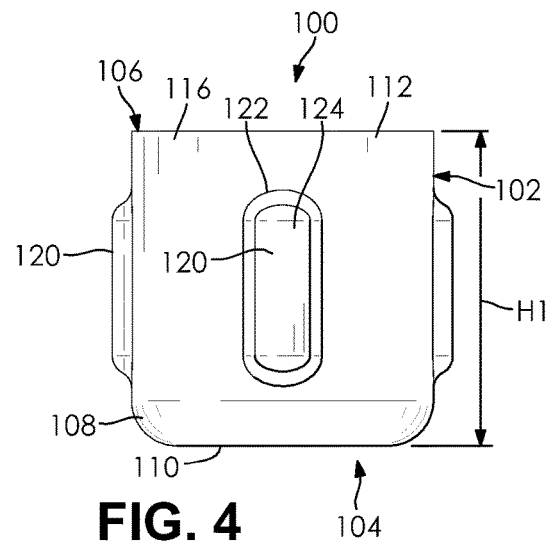
FIG. 4 is a rear elevational view of the insert shown in FIG. 1.
Figure 5:
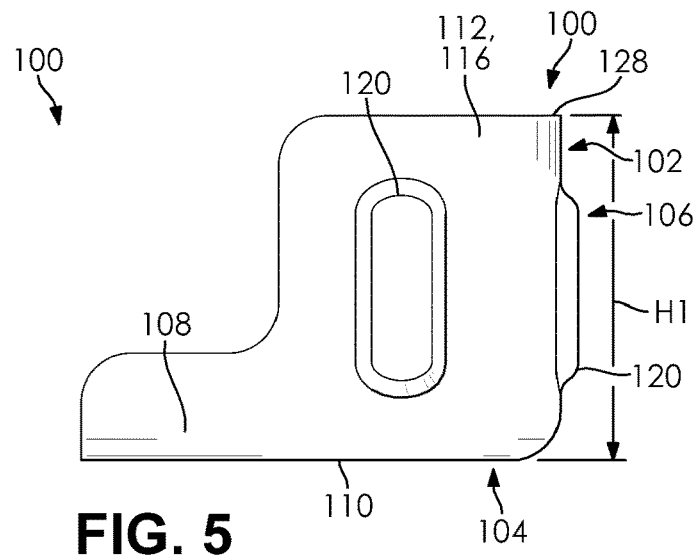
FIG. 5 is a side elevational view of the insert shown in FIG. 1.

The curved side wall 108 may also have a U-shaped profile, for example, as shown in FIG. 3. The U-shaped profile and the curved side wall 108 may together be configured to securely hold the AFO brace 101 within the heel portion 104, in operation. Additionally, the curved side wall 108 may provide reinforcement where the insert 102 is disposed within the shoe. Advantageously, the curved side wall 108 may militate against an undesirable amount of movement and friction between the AFO brace 101 and an interior surface of the shoe, which may also militate against a degradation of the interior surface of the shoe.

With renewed reference to FIGS. 1-12, the heel portion 104 may also have a bottom wall 110. The bottom wall 110 may be co-formed with the curved side wall 108. The curved side wall 108 may be disposed along a top edge of the bottom wall 110. The bottom wall 110 may have a length (L1). The length (L1) of the bottom wall 110 may be determined by a length (L2) of the AFO brace 101. The length (L1) will be less than or equal to the length (L2). More particularly, the length (L1) may be less than the length (L2). The bottom wall 110 may provide reinforcement where the insert 102 is disposed within the shoe. Advantageously, the bottom wall 110 may militate against friction between the AFO brace 101 and an interior surface of the shoe, which may militate against a degradation of the interior surface of the shoe.

Figure 1:
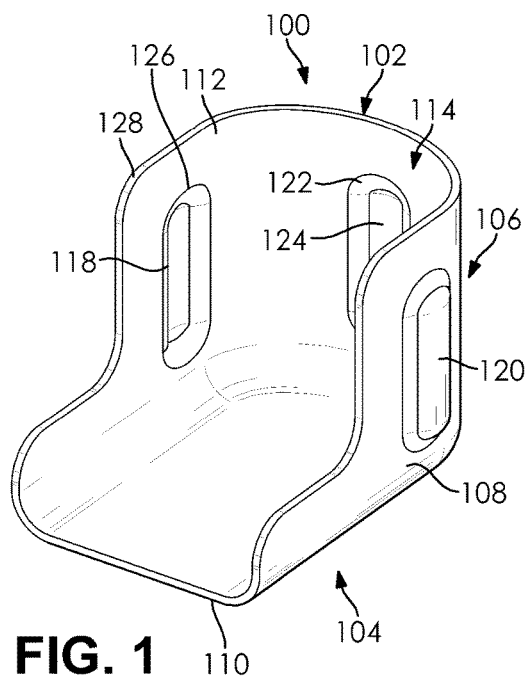
FIG. 1 is a top perspective view of an insert for a heel integration system, according to one embodiment of the present disclosure, and depicting the insert configured to be utilized with a high top shoe.
Figure 2:
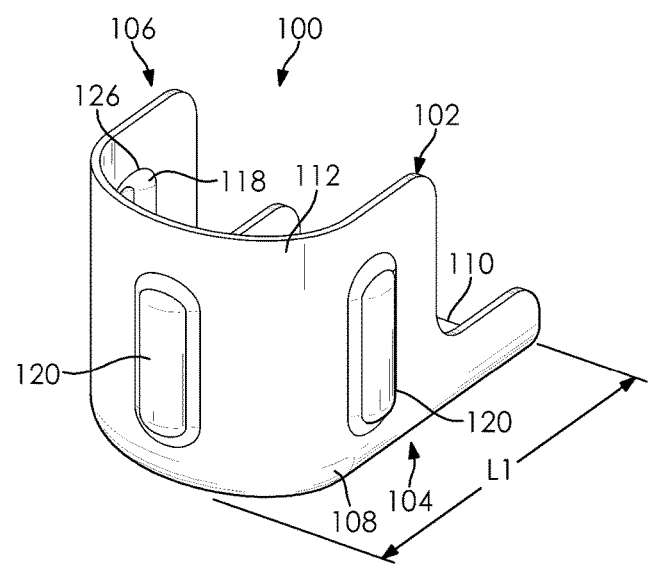
FIG. 2 is a rear perspective view of the insert shown in FIG. 1.

The ankle portion 106 may extend from a top edge of the heel portion 104. The ankle portion 106 may be defined by a curved wall 112. The curved wall 112 of the ankle portion 106 may have a U-shaped profile, for example, as shown in FIGS. 1-2. A curvature of the curved wall 112 of the ankle portion 106 may be configured to match a curvature of the ankle of the AFO brace 101.

The curved wall 112 of the ankle portion 106 may have a height (H1). The height (H1) may be determined by a height (H2) of the shoe. The height (H1) may be less than or equal to the height (H2), in order to militate against the insert 102 from undesirable extending out of the shoe 200, in operation. If the insert 102 were to protrude from the shoe 200, the insert 102 may be susceptible to cracking or otherwise becoming damaged, in operation. More particularly, where the insert 102 is configured to be disposed in a high top shoe or a boot, the height (H1) of the ankle portion 106 will be larger than the height (H1) of the ankle portion 106 of the insert 102 where it is configured to be disposed in a low top shoe. The curved wall 112 of the ankle portion 106 may have an interior surface 114 and an exterior surface 116.

In particular embodiments, at least one indentation 118 may be formed in the interior surface 114 of the ankle portion 106. In particular examples, as shown in FIGS. 1-12, the at least one indentation 118 includes a plurality of indentations 118. The indentations 118 may be capsule shaped, for example. The capsule shape may have an angled wall 122 and a base wall 124. A perimeter of the angled wall 122 may surround a perimeter of the base wall 124. The base wall 124 may be indented further into the interior surface 114 of the ankle portion 106 than the angled wall 122. It should be appreciated that the shape of the at least one indentation 118 may be determined by the particular AFO brace of the wearer. Accordingly, the at least one indentation 118 may have more than one angled wall 122 and more than one base wall 124 to accommodate particular AFO braces, for example, as shown in FIGS. 13-14. However, other suitable shapes for the at least one indentation 118 may also be employed, as desired.

The at least one indentation 118 may also have a corresponding protrusion 120. The protrusion 120 may extend outwardly from the exterior surface 116 of the ankle portion 106. The protrusion 120 may have a shape that corresponds substantially with the shape of the at least one indentation 118. The insert 102 may have multiple protrusions 120. The multiple protrusions 120 may cooperate with interior structures of the heel of the shoe. Advantageously, the cooperation protrusions 120 may provide a mechanical interference and, thus, may militate against an undesirable rotation of the insert 102 within the shoe 200, in operation. Accordingly, the projections 120 may evenly spaced about the ankle portion 106 to maximize the interference. In particular, the projections 120 may be arranged about 90 degrees apart from an other projection 120 on the ankle portion 106.

It should be appreciated that the at least one indentation 118 may be configured to receive a projection 103 of the AFO brace 101, for example, as shown in FIG. 9. The projections 103 may include hinges or ankle joints 105, such as those shown in the Hinged AFO brace 101 shown in FIGS. 13-14.

The at least one indentation 118 and the projection 103 of the AFO brace 101 may cooperate, in operation, to effectively lock or secure the AFO brace 101 within the insert 102 of the heel integration system 100. Accordingly, a location on the ankle portion 106 of the at least one indentation 118 may be determined by a number of projections 106 on the particular AFO brace of the wearer. Advantageously, the cooperation between the insert 102 and the AFO brace 101 allows the wearer to utilize shoes that more properly fit a size of the foot of the wearer. The at least one indentation 118 allows the insert 102 to accommodate excess bulk from the AFO brace 101 where the insert 102 is disposed in the shoe.

The cooperation of the at least one indentation 118 and the projection of the AFO brace 101 may involve one of a friction fit, a press fit, and a snap fit. In certain embodiments of the AFO brace 101, the projections 103 may be rubberized. Accordingly, the projections 103 of the AFO brace 101 and the at least one indentation 118 may form a friction fit automatically upon insertion of the AFO brace 101 into the insert 102. In other embodiments, the at least one indentation 118 may have a rubberized liner (not shown). Advantageously, the rubberized liner may optimize the secure fitting of the AFO brace 101 within the insert 102, in operation.

Accordingly, a particular shape of the at least one indentation 118 may be configured to match a shape of the projection 103 of the AFO brace 101 of the wearer in need of the heel integration system 100. As described hereinabove, the at least one indentation 118 may contain angled walls 122 and base walls 124 to accommodate AFO braces with projections 103 having additional projections 103 formed thereon, for example, as shown in FIGS. 13-14. Likewise, the AFO brace 101 may have multiple projections 103. Thus, the ankle portion 106 may have additional indentations 118 to accommodate the projections 103 of the AFO brace 101. For example, as shown in FIGS. 1-7, the ankle portion 106 may have a plurality of indentations 118 arranged about the inner surface 114.

As shown in FIGS. 1-7, the at least one indentation 118 may be oriented across the height (H1)) of the curved wall 112 of the ankle portion 106. Accordingly, a length (L3) of the at least one indentation 118 may be dependent on the height of the curved wall 112 of the ankle portion 106. For example, as shown in FIG. 1, the at least one indentation 118 may only partially extend along the height (H1)) of the curved wall 112, where the insert 102 is configured to be used with the high top shoe or the boot. In another example shown in FIG. 6, the at least one indentation 118 may extend an entirety of the height (H1)) of the curved wall 112 of the ankle portion 106, where the insert 102 is configured to be used in the low top shoe. Likewise, a length (L4) of the base wall 124 may extend to a top of the insert 102. A skilled artisan may select other suitable orientations for the at least one indentation 118, as desired.

In certain embodiments, the at least one indentation 118 may have a closed top 126, for example, as shown in FIGS. 1-5. The closed top 126 that may allow the AFO brace 101 to lock into place within the insert 102. Advantageously, the closed top may militate against the AFO brace 101 from sliding from the insert 102, in operation. The closed top 126 may be advantageous where utilized in the high top shoe or the boot.

With continued reference to FIGS. 1-5, the closed top embodiment may have the at least one indentation 118 entirely disposed along the height (H1)) of the ankle portion. In other words, the at least one indentation 118 does not extend to a top edge 128 of the ankle portion. The perimeter of the angled wall 122 may fully circumscribe the perimeter of the base wall 124.

Figure 6:
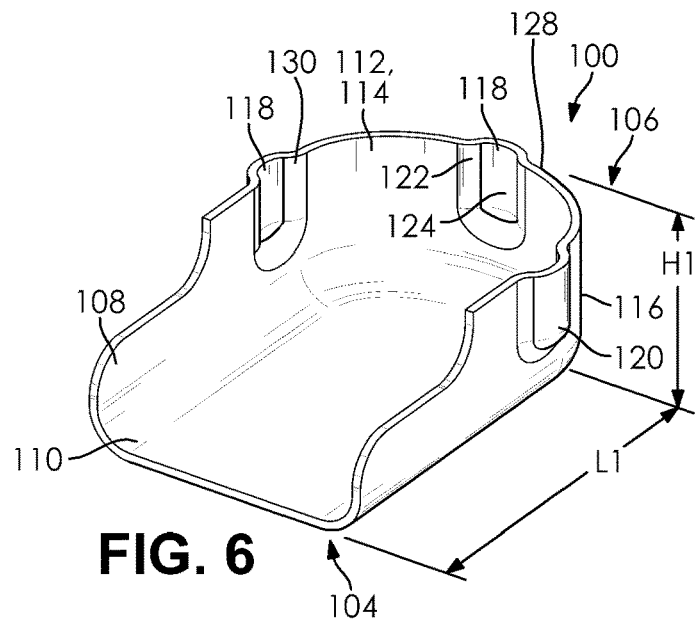
FIG. 6 is a top perspective view of the insert according to an additional embodiment of the present disclosure, and further depicting the insert where configured to be used with a low top shoe.
Figure 7:
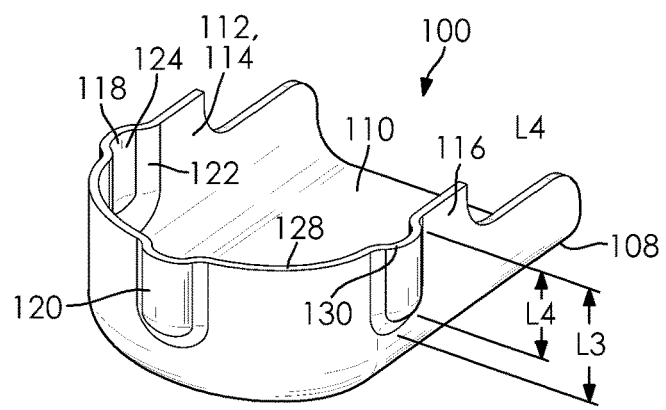
FIG. 7 is a rear perspective of the insert shown in FIG. 6.

In certain embodiments, the at least one indentation 118 may have an open top 130, for example, as shown in FIGS. 6-8. The open top 130 may allow for simpler insertion and removal of the AFO brace 101 compared to the closed top 126. The open top 128 may be advantageous where used in the low top shoe 200, as shown in FIG. 8.

With continued reference to FIGS. 6-8, the at least one indentation 118 may extend along the height (H1)) of the ankle portion 106 to the top edge 128 of the ankle portion 106. Likewise, each of the length (L3) of the angled wall 122 and a length (L4) of the base wall 124 may extend to the top edge 128 of the ankle portion. In other words, the at least one indentation 118 is "open" at the top edge 128 of the ankle portion 106. The perimeter of the base wall 124 is only partially circumscribed by the perimeter of the angled wall 122, where the insert 102 has an open top 130.

The present disclosure contemplates methods 400 of manufacturing the shoe with the heel integration system 100, for example, as shown in FIGS. 10-13. It should be appreciated that the method 400 may be utilized with an existing shoe 200, such that, the shoe may be modified to receive the insert 102. In other embodiments, the method 400 may be utilized to manufacture a shoe 200 with the heel integration system 100 preinstalled.

A first step 402 in the method 400 may include provision of measurements. The measurements may include at least one brace measurements and shoe measurements. The shoe measurements may include a length (L5) of the shoe 200. As described hereinabove, the relative size and shape of the insert 102 is dependent on the size and shape of the AFO brace 101 of the wearer, as well as the size and shape of the shoe the wearer would like to wear. Likewise, the first step 202 may require provision of at least one of a brand of the AFO brace 101 and a brand of the shoe within which the AFO brace 101 is to be inserted, along with the size measurements.

The measurements may be provided by the wearer directly to the manufacturer, for example, using a computer system configured to receive and store the brace measurements. The computer system for online orders may permit the wearer to submit predetermined measurements to the manufacturer over the Internet. The computer system may allow for the wearer to select a particular shoe design, while also providing the ability to upload all relevant measurements. The computer system may transmit this data to the manufacturer for order processing. For example, the computer system may include a server having a processor and a memory on which non-transitory processor-executable instructions are tangibly embodied, and a wearer computer from which a web application on the server may be accessed via the internet. Where the wearer computer is a mobile device, such as a smart phone, the computer system may also include a mobile application that may be downloaded to the mobile device through which the measurements may be supplied. A skilled artisan may employ other suitable computer systems and methods for facilitating the provision of measurements of the AFO brace 101 to be used with the heel integration system 100, as desired.

The method 400 may include a second step 404 of providing the shoe. As described hereinabove, the heel integration system 100 may be utilized with a variety of shoe types including the high top shoes such as boots, or the low top shoes such as sneakers. In certain embodiments, the shoe may be manufactured to accommodate the heel integration system 100 without additional modifications by the manufacturer.

A third step 406 in the method 400 may include a removing of padding from the heel portion 104 of the shoe, for example, as shown in FIGS. 10-12. The padding may be removed from an area that corresponds to a size and a shape of the insert 102 to be disposed within the shoe.

It should be appreciated that the padding from the heel portion 104 of the shoe is not necessary where the wearer is wearing the AFO brace 101. Accordingly, the padding may be removed in order to provide clearance for installation of the insert 102. The padding may include padding from walls of the heel of the shoe and padding from a sole portion of the shoe. Advantageously, the clearance provided by the step 406 of removing the padding, for example, as shown in FIG. 11, allows the insert 102 to be placed further into the heel of the shoe. Likewise, this allows the wearer to utilize shoes closer to the proper or preferred size of the wearer than if the insert 102 was not employed.

It should be appreciated that, in embodiments where the shoe is being manufactured with the insert 102, the padding is not removed. The shoe will be manufactured without padding in these embodiments, and otherwise is preconfigured for the installation of the insert 102.

The method 400 may have a fourth step 408 of providing the insert 102 as described hereinabove. The manufacturer may produce the insert 102 based on the supplied AFO brace 101 measurements and the measurements of the shoe. In some embodiments, a 3D printer may be utilized to produce the insert 102. In other embodiments, the insert 102 may be created from a mold. A skilled artisan may select other suitable methods of fabricating the insert 102, as desired.

The method 400 may have a fifth step 410 of installing the insert 102 in the shoe. More specifically, the insert 102 may be placed in the heel of the shoe where the padding has been removed. For example, the insert 102 may be placed in the shoe as shown in FIG. 8.

A sixth step 412 in the method 400 may include as securing of the insert 102 within the shoe. The manufacturer may secure the insert 102 via a plurality of suitable means including, but not limited to, stitches, adhesive, or other fastening means. In a most particular embodiment, for example as shown in FIG. 12, the insert 102 may be fastened to the shoe with stitches. A skilled artisan may select other suitable means for securing the insert 102 within the shoe, as desired.

With reference to FIGS. 8-9 and 12, the present disclosure further contemplates a combination 300 including the shoe 200 with the heel integration system 100 coupled thereto. More particularly, the shoe 200 may be manufactured via the method 200 described hereinabove.

It should be appreciated that the shoe of the combination 300 may be designed in a variety of styles. The shoe may be configured to the dimensions of the AFO brace 101 of the wearer, as described hereinabove. The shoe 200 may be manufactured from conventional materials and methods. A skilled artisan may select suitable materials for the shoe, as desired.

With continued reference to FIG. 9, the combination 300 may have the insert 102 affixed to a heel of the shoe 200. The shoe 200 may have substantially no padding 302 at the heel. More particularly, the heel of the shoe may not have padding 302 in an area covered by the insert 102. The shoe may have padding 302 disposed in a sole of the shoe 200. The padding 302 of the sole may run from a toe of the shoe 200 to the bottom wall 110 of the insert 102.

In operation, the wearer may utilize the shoe 200 with the heel integration system 100 in a manner similar to a conventional shoe. The wearer may place a foot with the AFO brace 101 into the shoe. The projections 103 of the AFO brace 101 will slide into the at least one recess 118 of the insert 102 that is preinstalled in the shoe. When the wearer removes the foot with the AFO brace 101, the insert 102 remains in the shoe.

Advantageously, the heel integration system 100 of the present disclosure allows wearers with AFO braces 101 to utilized properly sized shoes. It should be appreciated that the insert 102 of the present disclosure provides clearance within the shoe for the AFO brace 101. Additionally, the insert 102 of the heel integration system 100 may militate against damage to the interior of the shoe that may otherwise be caused by friction between the AFO brace 101 and the shoe where the insert 102 is not utilized.

While certain representative embodiments and details have been shown for purposes of illustrating the invention, it will be apparent to those skilled in the art that various changes may be made without departing from the scope of the disclosure, which is further described in the following appended claims.

What is claimed is:

1. A combination, comprising:
   a shoe having an upper and a sole, wherein the shoe is configured to cover an instep of a foot of a wearer; and
   a heel integration system including an insert having a front end and a back end, the insert configured to be disposed in the shoe, and configured to receive an ankle-foot orthoses brace while the shoe is worn, the insert having a heel portion and an ankle portion, the ankle portion having a curved wall with at least one bulge formed therein,
   wherein the bulge is created from an indentation formed on an interior surface of the ankle portion which forms a protrusion on an exterior surface of the ankle portion,
   wherein the indentation is configured to receive at least one projection of the Ankle-foot orthoses brace,
   wherein the protrusion is disposed directly adjacent to the indentation,
   wherein the protrusion has a shape that corresponds with a shape of the indentation, and
   wherein the at least one bulge is formed in the curved wall of the ankle portion at the back end of the insert.

2. The combination of claim 1, wherein a heel of the shoe has substantially no padding.

3. The combination of claim 1, wherein the sole of the shoe has padding that extends from a toe of the shoe to the insert.

4. The combination of claim 1, wherein the insert is affixed to the shoe via stitching.

5. The heel integration system of claim 1, wherein the curved wall of the ankle portion is disposed on a top edge of a curved side wall of the heel portion, and the curved wall has a U-shaped profile, the insert has an L-shaped cross section.

6. The combination of claim 1, wherein the heel portion of the insert has a bottom wall co-formed with a curved side wall, the at least one recess is capsule shaped, and the at least one recess is disposed along a height of the ankle portion.

* * * * *